(12) United States Patent
Nakamura et al.

(10) Patent No.: US 9,035,103 B2
(45) Date of Patent: May 19, 2015

(54) OPTICAL RESOLUTION METHODS FOR BICYCLIC COMPOUNDS USING ASYMMETRIC CATALYSTS

(71) Applicant: Daiichi Sankyo Company, Limited, Tokyo (JP)

(72) Inventors: Yoshitaka Nakamura, Kanagawa (JP); Takafumi Kitawaki, Kanagawa (JP); Takeshi Kaneda, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 14/300,924

(22) Filed: Jun. 10, 2014

(65) Prior Publication Data
US 2014/0296569 A1 Oct. 2, 2014

Related U.S. Application Data

(63) Continuation of application No. PCT/JP2012/082355, filed on Dec. 13, 2012.

(30) Foreign Application Priority Data

Dec. 15, 2011 (JP) .................... 2011-274965

(51) Int. Cl.
*C07C 49/593* (2006.01)
*C07C 49/627* (2006.01)
*C07C 45/80* (2006.01)
*C07C 45/85* (2006.01)
*C07B 57/00* (2006.01)
*C07C 227/12* (2006.01)

(52) U.S. Cl.
CPC ............. *C07C 45/80* (2013.01); *C07B 57/00* (2013.01); *C07C 227/12* (2013.01); *C07C 45/85* (2013.01); *C07C 2102/20* (2013.01)

(58) Field of Classification Search
CPC ...... C07C 49/593; C07C 49/627; C07C 45/80; C07C 45/85
USPC ........................................... 568/374
See application file for complete search history.

(56) References Cited

U.S. PATENT DOCUMENTS

| 8,324,425 | B2 | 12/2012 | Kitagawa et al. |
| 2003/0078300 | A1 | 4/2003 | Blakemore et al. |
| 2003/0220397 | A1 | 11/2003 | Bryans et al. |
| 2004/0152779 | A1 | 8/2004 | Bryans et al. |
| 2006/0154929 | A1 | 7/2006 | Anker et al. |
| 2010/0249229 | A1 | 9/2010 | Shimada et al. |
| 2014/0094624 | A1* | 4/2014 | Nakamura et al. ............ 562/501 |

FOREIGN PATENT DOCUMENTS

| JP | 60-169434 | 9/1985 |
| WO | WO 2010/110361 A1 | 9/2010 |
| WO | WO 2012/169474 A1 | 12/2012 |
| WO | WO 2012169474 A1 * | 12/2012 |

OTHER PUBLICATIONS

Bryans et al., "Identification of Novel Ligands for the Gabapentin Binding Site on the $\alpha_2\delta$ Subunit of a Calcium Channel and Their Evaluation as Anticonvulsant Agents," *J. Med. Chem.*, (1998), 41:1838-1845.

Gee et al., "The Novel Anticonvulsant Drug, Gabapentin (Neurontin), Binds to the Subunit of a Calcium Channel," *J. Biol. Chem.*, (1996), 271(10):5768-5776.

Marotta et al., "A New, Effective Route to Methyl Substituted 3,3a,4,6a-Tetrahydro-2*H*-cyclopenta[*b*]furan-2-ones," *Tetrahedron Letters*, (1994), 35(18):2949-2950.

Mathew et al., "Amplification of Enantiomeric Excess in a Proline-Mediated Reaction," *Angew. Chem. Int. Ed.*, (2004), 43:3317-3321.

International Search Report issued in PCT Application No. PCT/JP2012/082355 on Mar. 12, 2013, 2 pages.

International Preliminary Report on Patentability issued in PCT Application No. PCT/JP2012/082355 on Mar. 12, 2013, 4 pages.

* cited by examiner

*Primary Examiner* — Yevegeny Valenrod

(74) *Attorney, Agent, or Firm* — Dorsey and Whitney LLP

(57) ABSTRACT

An optically active bicyclic compound is efficiently produced by optical resolution using an optically active amine.

18 Claims, No Drawings

OPTICAL RESOLUTION METHODS FOR BICYCLIC COMPOUNDS USING ASYMMETRIC CATALYSTS

This application claims the benefit under 35 U.S.C. §111 (a) as a continuation application of International Application No. PCT/JP2012/082355, filed Dec. 13, 2012, entitled "Optical Resolution Method for Bicyclic Compound Using Asymmetric Catalyst," which claims priority to Japanese Patent Application No. 2011-274965, filed Dec. 15, 2011.

TECHNICAL FIELD

The present invention relates to a producing method for an optically active bicyclic γ-amino acid derivative or a pharmacologically acceptable salt thereof, particularly, a compound having activity as an $\alpha_2\delta$ ligand and an intermediate thereof.

BACKGROUND ART

Compounds that exhibit high-affinity binding to voltage-dependent calcium channel subunit $\alpha_2\delta$ have been shown to be effective for treating, for example, neuropathic pain (see e.g., Non-patent Literatures 1 and 2).

Several types of $\alpha_2\delta$ ligands are currently known as therapeutic drugs for neuropathic pain. Examples of $\alpha_2\delta$ ligands include gabapentine and pregabalin. $\alpha_2\delta$ ligands such as these compounds are useful for treating epilepsy and neuropathic pain or the like (e.g., Patent Literature 1). Other compounds are disclosed in, for example, Patent Literatures 2, 3, and 4.

Also, the present applicant has previously reported an $\alpha_2\delta$ ligand and a method for producing the same in Patent Literatures 5 and 6.

CITATION LIST

Patent Literature

Patent Literature 1: US 2006/154929
Patent Literature 2: US 2003/220397
Patent Literature 3: US 2004/152779
Patent Literature 4: US 2003/78300
Patent Literature 5: US 2010/249229
Patent Literature 6: US 2010/110361

Non-Patent Literature

Non-patent Literature 1: J Biol. Chem. 271 (10): 5768-5776, 1996
Non-patent Literature 2: J Med. Chem. 41: 1838-1845, 1998

SUMMARY OF INVENTION

Technical Problem

An object of the present invention is to provide a production method for an optically active bicyclic γ-amino acid derivative or a pharmacologically acceptable salt thereof, particularly, a compound having activity as an $\alpha_2\delta$ ligand and an intermediate thereof.

Patent Literature 5 or 6 has reported a method for producing compound 6 as described in Scheme 1.

Focusing on a stereocontrol method for an asymmetric carbon in the method for producing compound 6, the present inventors have continued diligent studies to develop an efficient method therefor. In the previous production method, optical resolution is performed in a step (Step 4) immediately prior to the final step. The present inventors, however, have hypothesized that a more efficient production method would be established by carrying out the optical resolution in an earlier step.

Specifically, a technical problem to be solved by the present invention is to develop a production method which involves preparing an intermediate of compound 6 as an optically active compound in an earlier step in the production of compound 6. The present inventors have continued diligent studies to solve this problem and consequently completed the present invention by solving the problem.

Scheme 1

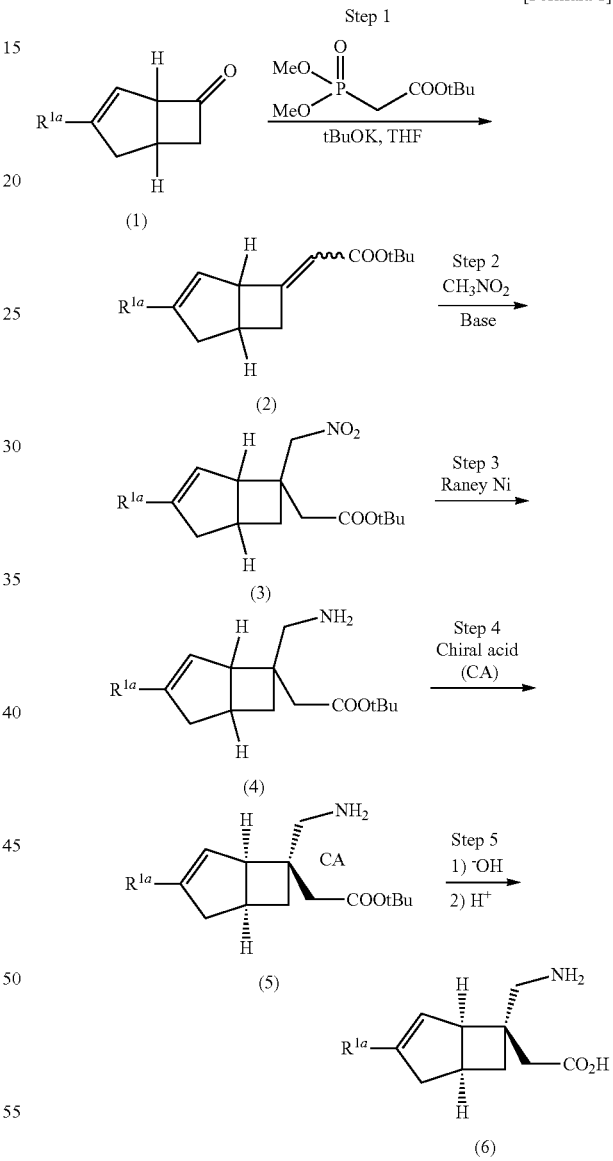

[Formula 1]

wherein the substituent is defined as follows: $R^{1a}$: a hydrogen atom or a C1-C6 alkyl group.

Solution to Problem

The present invention will be described below.

[1] A method for producing a compound represented by the general formula (I) or a compound represented by the general formula (II):

[Formula 2]

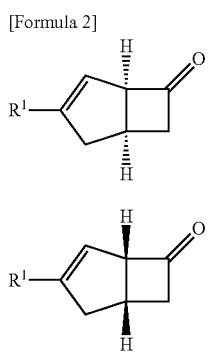

the method comprising (1) reacting a racemic mixture of the compound represented by the general formula (I) and the compound represented by the general formula (II) with a compound represented by the general formula (III) in the presence of an optically active amine and a solvent to convert either the compound represented by the general formula (I) or the compound represented by the general formula (II) to a compound represented by the general formula (I') and a compound represented by the general formula (I") or to a compound represented by the general formula (II') and a compound represented by the general formula (II"):

[Formula 3]

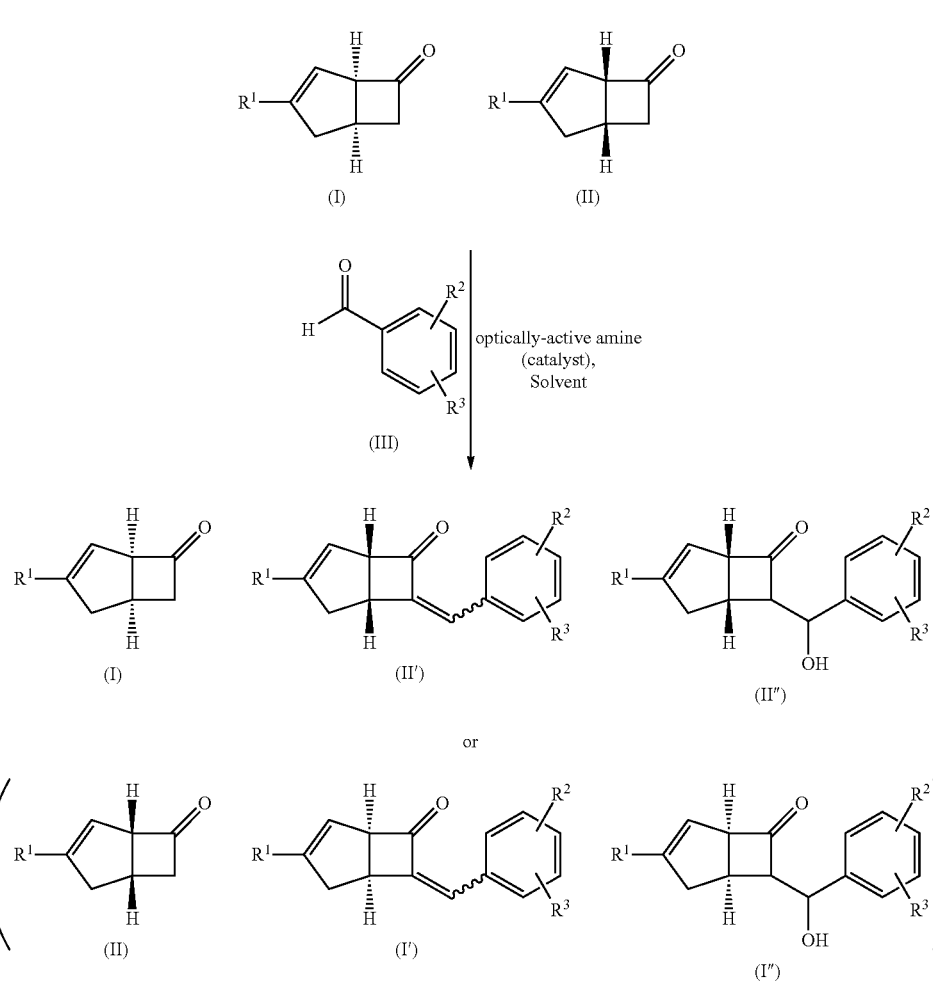

and then (2) separating the compound represented by the general formula (I) from the compound represented by the general formula (II') and the compound represented by the general formula (II") or separating the compound represented by the general formula (II) from the compound represented by the general formula (I') and the compound represented by the general formula (I") to produce the compound represented by the general formula (I) or the compound represented by the general formula (II):

[Formula 4]

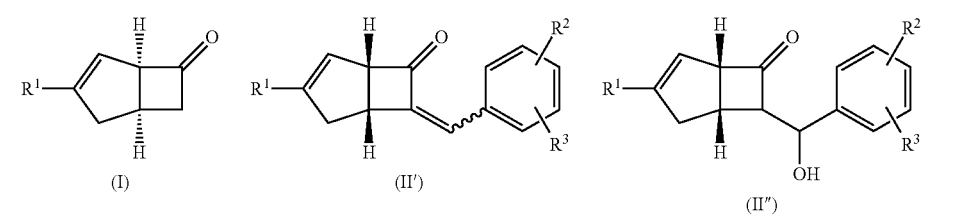

or

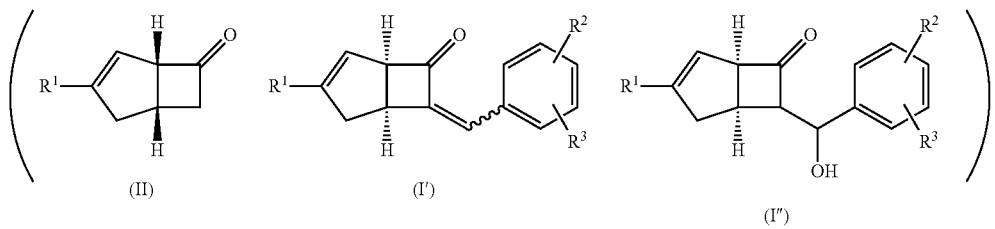

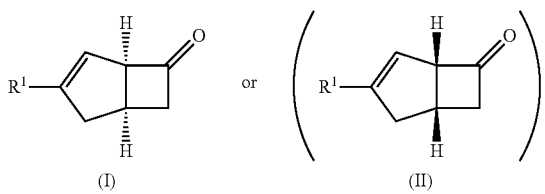

wherein the substituents are defined as follows: $R^1$: a hydrogen atom or a C1-C6 alkyl group; and $R^2$ and $R^3$ are the same or different and each is a group selected from a hydrogen atom, a halogen atom, a nitro group, and a carboxy group.

Preferred aspects of the present invention are as described below.

[2] A method for producing a compound represented by the general formula (I):

[Formula 5]

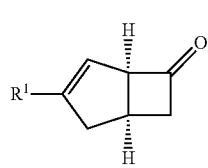

the method comprising (1) reacting a racemic mixture of the compound represented by the general formula (I) and a compound represented by the general formula (II) with a compound represented by the general formula (III) in the presence of an optically active amine and a solvent to convert the compound represented by the general formula (II) to a compound represented by the general formula (II') and a compound represented by the general formula (II"):

[Formula 6]

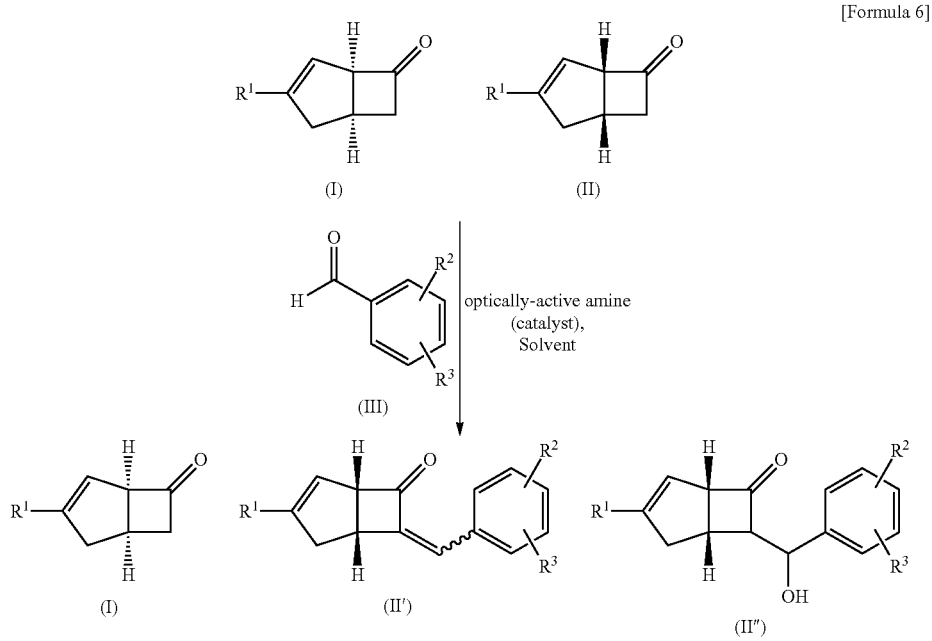

and then (2) separating the compound represented by the general formula (I) from the compound represented by the general formula (II') and the compound represented by the general formula (II'') to produce the compound represented by the general formula (I):

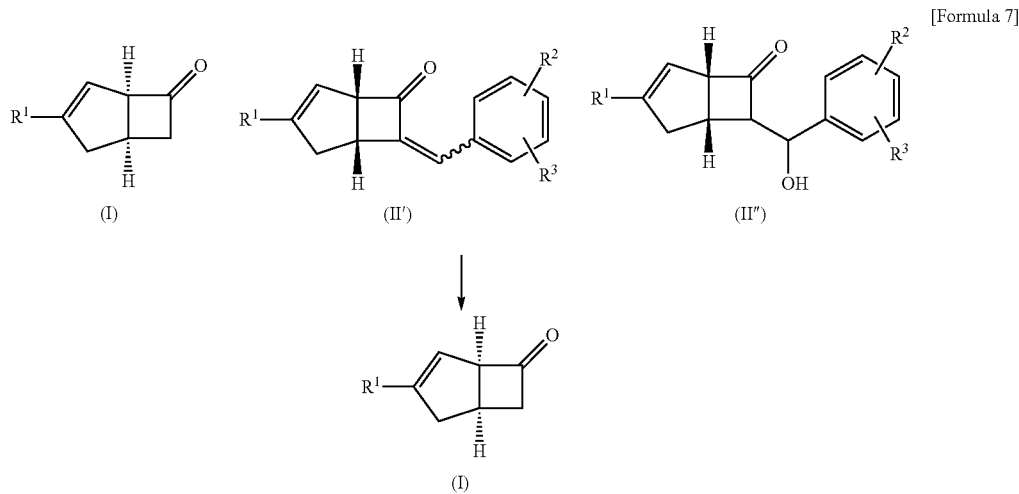

wherein the substituents are defined as follows: $R^1$: a hydrogen atom or a C1-C6 alkyl group; and $R^2$ and $R^3$ are the same or different and each is a group selected from a hydrogen atom, a halogen atom, a nitro group, and a carboxy group.

[3] The method according to [1] or [2], wherein $R^1$ is a hydrogen atom, a methyl group, or an ethyl group.

[4] The method according to any one of [1] to [3], wherein $R^2$ is a hydrogen atom, and $R^3$ is a carboxy group.

[5] The method according to any one of [1] to [4], wherein the compound represented by the general formula (III) is used in (1) in an amount of 0.5 to 2.0 equivalents with respect to the racemic mixture of the compound represented by the general formula (I) and the compound represented by the general formula (II).

[6] The method according to any one of [2] to [5], wherein the optically active amine in (1) is any one amine selected from the following group:

[Formula 7]

[Formula 8]

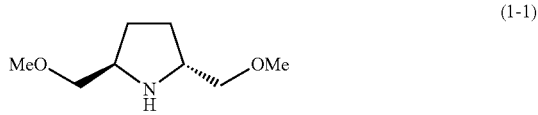

(1-1)

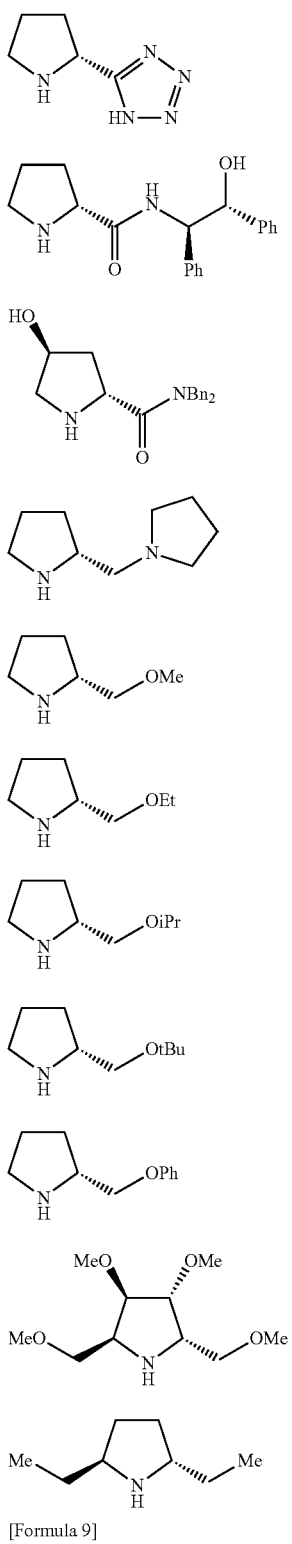
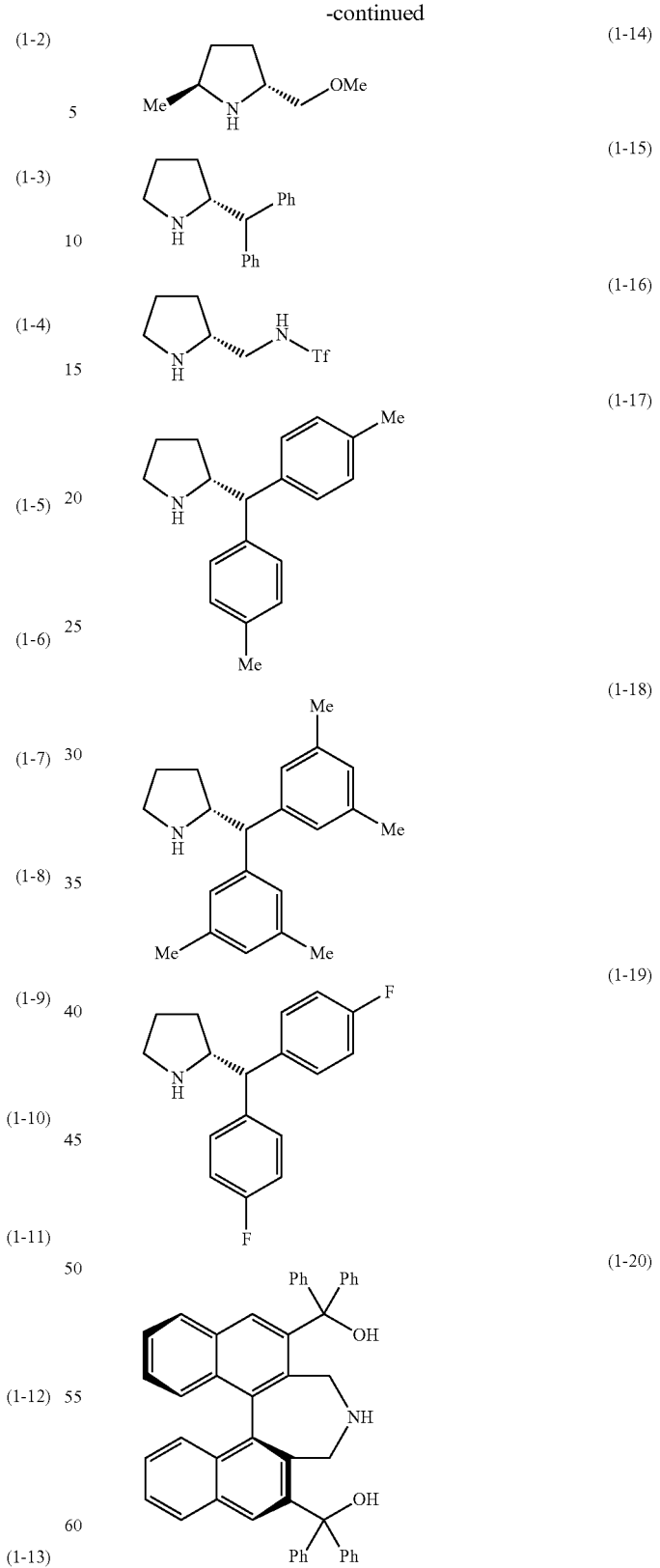
wherein the symbols represent substituents defined as follows:
Me: a methyl group, Ph: a phenyl group, Bn: a benzyl group, Et: an ethyl group, iPr: an isopropyl group, tBu: a tertiary butyl group, and Tf: a trifluoromethanesulfonyl group.

[7] The method according to any one of [1] to [6], wherein the optically active amine is used in (1) in an amount of 0.01 to 0.3 equivalents with respect to the racemic mixture of the compound represented by the general formula (I) and the compound represented by the general formula (II).

[8] The method according to any one of [1] to [7], wherein the solvent in (1) is any one solvent selected from the following group:

acetonitrile, 2-propanol, tetrahydrofuran, 1,2-dimethoxyethane, dimethylacetamide, dimethylformamide, N-methyl-2-pyrrolidone, 1,3-dimethyl-2-imidazolidinone, and dimethyl sulfoxide.

[9] The method according to any one of [1] to [8], wherein a base is further used in (1).

[10] The method according to [9], wherein the base used is any one base selected from the following group:

potassium phosphate, triethylamine, tributylamine, diisopropylethylamine, 4-methylmorpholine, pyridine, tetramethylethylenediamine, N-methylimidazole, 1,8-diazabicyclo[5.4.0]undec-7-ene, 1,4-diazabicyclo[2.2.2]octane, 4-picoline, 2,6-lutidine, N-methylpyrrole, N-methylpyrrolidine, N-methylpiperidine, and diethylaniline.

[11] A method for producing a compound represented by the general formula (IV) or a salt thereof, comprising using a compound represented by the general formula (I) produced by a method according to any one of [2] to [10]:

[Formula 10]

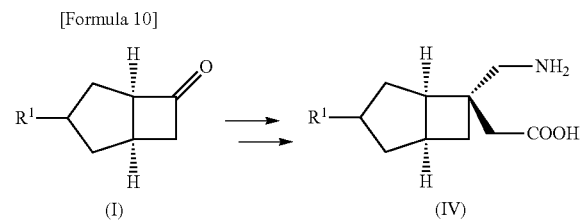

Advantageous Effects of Invention

The present invention is useful for producing an optically active bicyclic γ-amino acid derivative or a pharmacologically acceptable salt thereof, particularly, a compound having activity as an α2δ ligand and an intermediate thereof.

The production method of the present invention involves preparing an intermediate as an optically active compound in an earlier step in the production and as such, is efficient.

In addition, a purification step can be performed more efficiently by virtue of a carboxy group contained in a compound represented by the general formula (III).

DESCRIPTION OF EMBODIMENTS

A C1-C6 alkyl group refers to a linear or branched alkyl group having 1 to 6 carbon atoms and includes, for example, a methyl group, an ethyl group, a propyl group, an isopropyl group, a butyl group, an isobutyl group, a sec-butyl group, a pentyl group, and a hexyl group. A methyl group, an ethyl group, or a propyl group is preferred.

A halogen atom refers to a fluorine atom, a chlorine atom, a bromine atom, and an iodine atom. A chlorine atom is preferred.

A compound represented by the general formula (I) or the general formula (II) is preferably a compound wherein $R^1$ is a hydrogen atom, a methyl group, or an ethyl group.

[Formula 11]

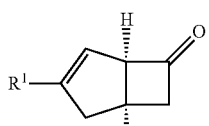

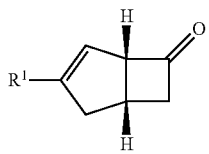

A compound represented by the general formula (III) is preferably a compound wherein $R^2$ is a hydrogen atom or a chlorine atom, and $R^3$ is a chlorine atom, a nitro group, or a carboxy group.

[Formula 12]

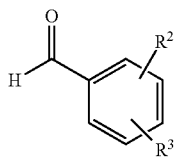

The compound represented by the general formula (III) is more preferably 4-nitrobenzaldehyde, 2,4-dichlorobenzaldehyde, or 4-formylbenzoic acid, particularly preferably 4-formylbenzoic acid. The presence of the carboxyl group in the compound represented by the general formula (III) allows unnecessary reactants or aldol addition products to be removed into an aqueous layer by merely washing an organic layer with an aqueous alkali solution after completion of the reaction. Thus, a highly pure and optically active compound represented by the general formula (I) or the general formula (II) can be efficiently obtained by a convenient operation.

The compound represented by the general formula (III) is used in an amount of preferably 0.5 to 2.0 equivalents, more preferably 0.8 to 1.2 equivalents, with respect to the racemic mixture of the compound represented by the general formula (I) and the compound represented by the general formula (II).

In the present invention, the "optically active amine" used for producing the compound represented by the general formula (I) is preferably an optically active 2-substituted pyrrolidine derivative or an amine catalyst having a binaphthyl skeleton, as shown below in Table 1. In this context, an enantiomer having a configuration opposite to the optically active amine used for producing the compound represented by the general formula (I) may be used in the production of the compound represented by the general formula (II).

The optically active amine is used in an amount of preferably 0.01 to 0.3 equivalents, more preferably 0.05 to 0.15 equivalents, with respect to the racemic mixture of the compound represented by the general formula (I) and the compound represented by the general formula (II).

TABLE 1
[Formula 13]
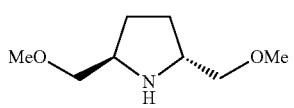 [SMILES: COC[C@H]1CC[C@H](COC)N1] (1-1)
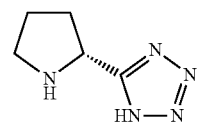 (1-2)
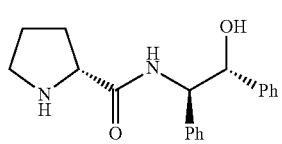 [SMILES: O=C(N[C@H](c1ccccc1)[C@H](O)c1ccccc1)[C@H]1CCCN1] (1-3)
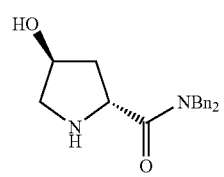 (1-4)
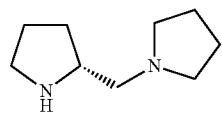 [SMILES: C1CN[C@@H](CN2CCCC2)C1] (1-5)
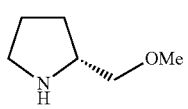 (1-6)
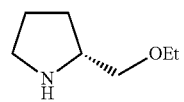 (1-7)
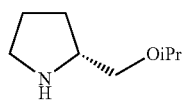 (1-8)
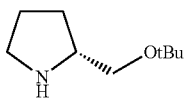 (1-9)
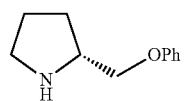 [SMILES: c1ccc(OC[C@H]2CCCN2)cc1] (1-10)
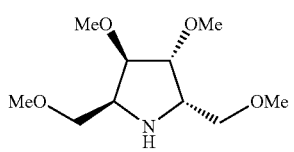 [SMILES: COC[C@@H]1N[C@@H](COC)[C@@H](OC)[C@@H]1OC] (1-11)
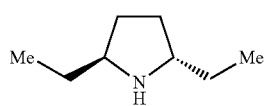 (1-12)
TABLE 1-continued
[Formula 14]
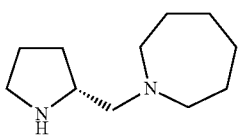 [SMILES: C1CCCN(C[C@H]2CCCN2)CC1] (1-13)
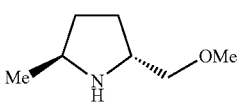 (1-14)
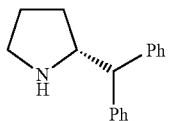 (1-15)
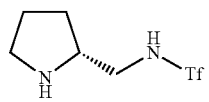 (1-16)
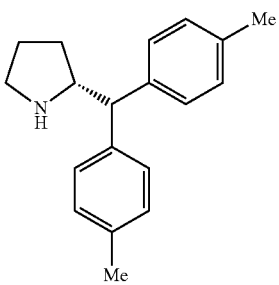 [SMILES: Cc1ccc(C(c2ccc(C)cc2)[C@H]2CCCN2)cc1] (1-17)
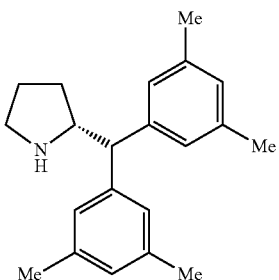 [SMILES: Cc1cc(C)cc(C(c2cc(C)cc(C)c2)[C@H]2CCCN2)c1] (1-18)
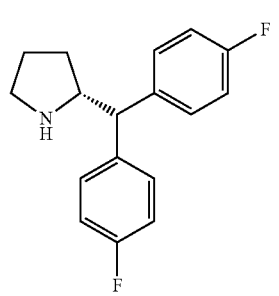 [SMILES: Fc1ccc(C(c2ccc(F)cc2)[C@H]2CCCN2)cc1] (1-19)

TABLE 1-continued

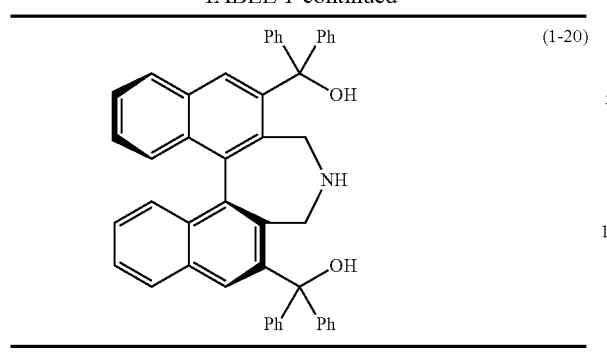

The following optically active amines are further preferred:
(R,R)-2,5-bis(methoxymethyl)pyrrolidine,
(R)-(2-pyrrolidinyl)-1H-tetrazole,
(R)-2-(methoxymethyl)pyrrolidine,
(R)-2-(ethoxymethyl)pyrrolidine,
(R)-2-(isopropoxymethyl)pyrrolidine,
(R)-2-(t-butoxymethyl)pyrrolidine,
(R)-2-(phenoxymethyl)pyrrolidine,
(R)-diphenylmethylpyrrolidine,
N-[(2R)-2-pyrrolidinylmethyl]-trifluoromethanesulfonamide,
(R)-2-[bis(4-methylphenyl)methyl]pyrrolidine,
(R)-2-[bis(3,5-dimethylphenyl)methyl]pyrrolidine,
(R)-2-[bis(4-fluorophenyl)methyl]pyrrolidine, or
(S)-4,5-dihydro-3H-dinaphtho[2,1-c:1',2'-e]azepine-2,6-diylbis(diphenylmethanol).

The optically active amine is particularly preferably
(R,R)-2,5-bis(methoxymethyl)pyrrolidine or
(R)-diphenylmethylpyrrolidine.

The enantiomer of the optically active amine can be appropriately selected for use in the production of the compound represented by the general formula (I) or the compound represented by the general formula (II).

The solvent is preferably a highly polar solvent such as acetonitrile, 2-propanol, tetrahydrofuran, 1,2-dimethoxyethane, dimethylacetamide, dimethylformamide, N-methyl-2-pyrrolidone, 1,3-dimethyl-2-imidazolidinone, or dimethyl sulfoxide, more preferably tetrahydrofuran, dimethylacetamide, dimethylformamide, or N-methyl-2-pyrrolidone.

The base is preferably potassium phosphate, triethylamine, tributylamine, diisopropylethylamine, 4-methylmorpholine, pyridine, tetramethylethylenediamine, N-methylimidazole, 1,8-diazabicyclo[5.4.0]undec-7-ene, 1,4-diazabicyclo[2.2.2]octane, 4-picoline, 2,6-lutidine, N-methylpyrrole, N-methylpyrrolidine, N-methylpiperidine, or diethylaniline, more preferably 4-methylmorpholine, pyridine, N-methylimidazole, 4-picoline, or N-methylpiperidine.

The reaction temperature is preferably 20 to 80° C., more preferably 30 to 50° C.

A compound represented by the general formula (IV) or the general formula (IV') can be produced in the same way as in a production method described in Patent Literature 6 (WO 2010/110361) above using the compound represented by the general formula (I) or the compound represented by the general formula (II).

[Formula 15]

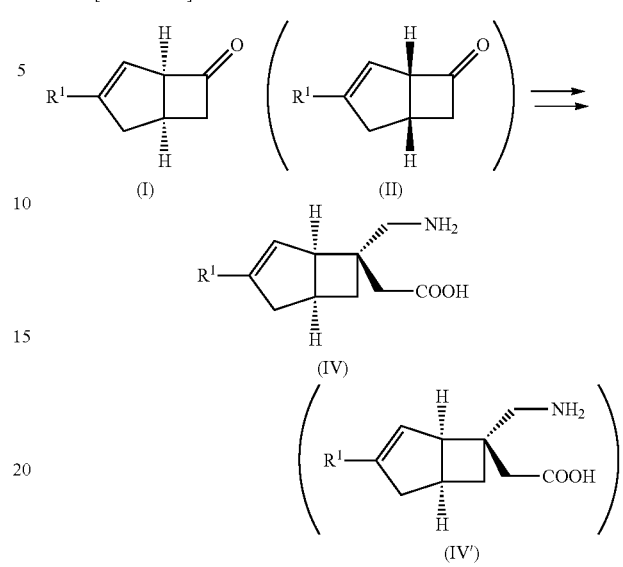

Since compounds represented by the general formula (IV), or the like form salts through reaction with an acid or a base by having amino and carboxyl groups in the structure, a "salt" as used herein refers to these salts.

The compound represented by the general formula (IV), or the like, when left in the air or recrystallized, may associate with adsorbed water through water absorption to form a hydrate. Such hydrates are also encompassed by the salts of the present invention.

The compound represented by the general formula (IV) or a salt thereof exhibits activity as an $\alpha_2\delta$ ligand and affinity for voltage-dependent calcium channel subunit $\alpha_2\delta$ and is useful as an active ingredient in a pharmaceutical composition used for treating and/or preventing pain, central nervous system involvement, and other disorders.

EXAMPLES

Example 1

(1R,5S)-3-Ethylbicyclo[3.2.0]hept-3-en-6-one

[Formula 16]

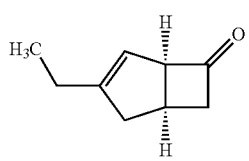

4-Formylbenzoic acid (22.1 g) and 4-methylmorpholine (16.3 g) were dissolved in N-methyl-2-pyrrolidone (60 mL). A racemic mixture (20.0 g) of 3-ethylbicyclo[3.2.0]hept-3-en-6-one and (R)-diphenylmethylpyrrolidine hydrochloride (4.02 g) were added to the solution.

The reaction mixture was heated to 40° C., stirred for 20 hours, and cooled to room temperature. Methyl t-butyl ether (100 mL) and a 1 mol/l aqueous hydrochloric acid solution (140 mL) were added to the reaction mixture. The mixture was vigorously stirred to separate an organic layer. Again, the aqueous layer was subjected to extraction with methyl t-butyl ether (100 mL). The organic layers were combined, and water (200 mL) and sodium bicarbonate (18.5 g) were added thereto. The mixture was vigorously stirred to separate an organic layer.

The organic layer was washed with a 5% aqueous sodium bicarbonate solution (50 mL) and concentrated. The obtained residue was distilled under reduced pressure to obtain 7.84 g of the title compound (39%, 98% ee) as a colorless oil.

Example 2

(1R,5S)-3-Ethylbicyclo[3.2.0]hept-3-en-6-one

[Formula 17]

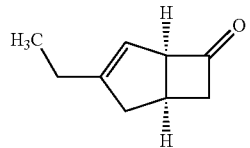

4-Formylbenzoic acid (110 g) and 4-methylmorpholine (74.3 g) were added to a solution of a racemic mixture (100 g) of 3-ethylbicyclo[3.2.0]hept-3-en-6-one in N-methyl-2-pyrrolidone (300 mL). Then, (R,R)-(−)-2,5-bis(methoxymethyl)pyrrolidine (11.7 g) was added to the mixture.

The reaction mixture was heated to 40° C., stirred for 28 hours, then cooled to room temperature, and further stirred for 12 hours. The reaction mixture was cooled to 10° C., and hexane (500 mL) and a 5% aqueous sodium bicarbonate solution (700 mL) were added thereto. The mixture was vigorously stirred to separate an organic layer. The aqueous layer was subjected to extraction with hexane (200 mL) three times. The organic layers were combined. The combined organic layer was washed with water (200 mL) and concentrated. The obtained residue was distilled under reduced pressure to obtain 45.3 g of the title compound (45%, 97% ee) as a colorless oil.

Example 3

Method for Analyzing Optical Purity of 3-ethylbicyclo[3.2.0]hept-3-en-6-one

The abundance ratios of the (1R,5S)-3-ethylbicyclo[3.2.0]hept-3-en-6-one (hereinafter, referred to as RS-isomer) obtained in Examples 1 and 2 and an optical isomer having a configuration opposite thereto (hereinafter, referred to as SR-isomer) were determined by gas chromatography analysis under conditions as shown below.

Column: Cyclosil-B (0.25 mm×30 m, DF=0.25 mm)
Detector: FID
Temperature of inlet: 230° C.
Temperature of vaporizing chamber: 230° C.
Temperature of oven: 130° C. (0-13 min)→20° C./min→230° C. (18-20 min)
Flow rate: 1.5 mL/min (He)
Injection quantity: 1 μL
Analysis time: 20 min
Preparation of sample: 10 mL of a reaction solution was separated into aqueous and organic layers with hexane/5% NaHCO3 aq., and the obtained hexane layer was used in the analysis.

ee %: {[(RS-isomer area)−(SR-isomer area)]/[(RS-isomer area)+(SR-isomer area)]}×100

Retention time: RS-isomer: approximately 7.1 min, SR-isomer: approximately 8.2 min

The invention claimed is:
1. A method of producing a compound of formula (I) or a compound of formula (II):

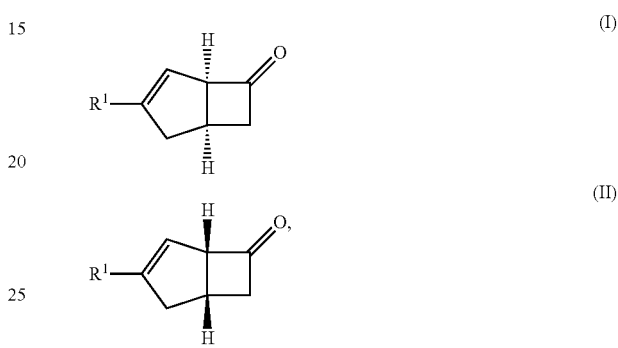

comprising:
reacting a racemic mixture of the compound of formula (I) and the compound of formula (II) with a compound of formula (III) in the presence of an optically active amine and a solvent to convert either the compound of formula (I) or the compound of formula (II) to a compound of formula (I') and a compound of formula (I'') or to a compound of formula (II') and a compound of formula (II''):

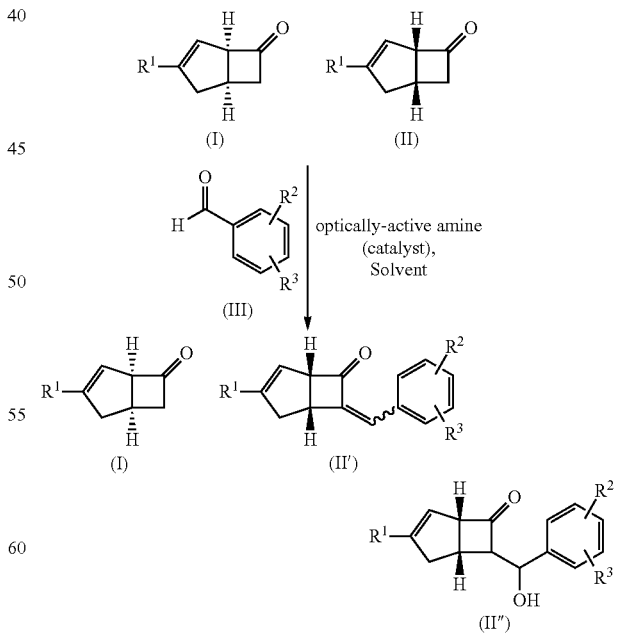

or

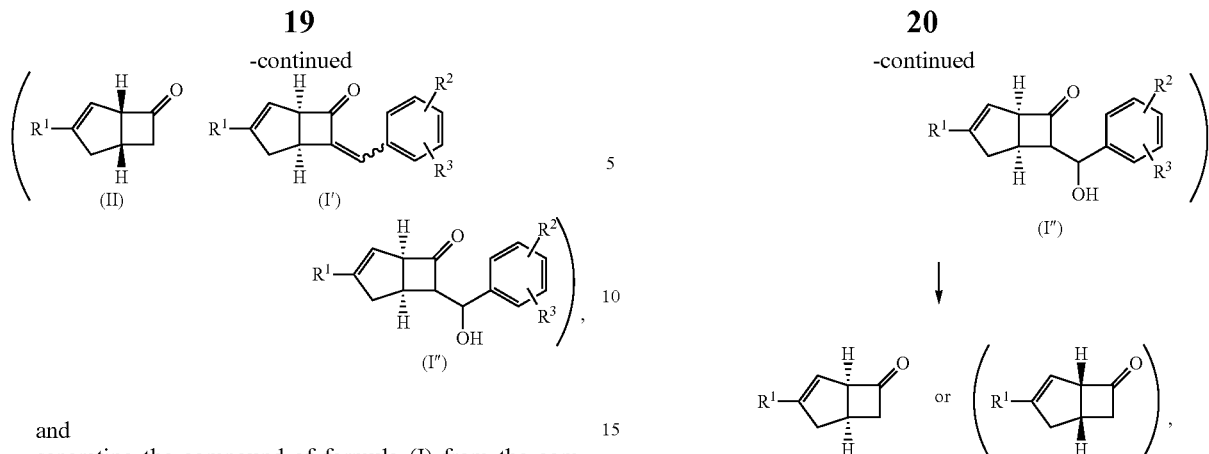

and separating the compound of formula (I) from the compound of formula (II') and the compound of formula (II'') or separating the compound of formula (II) from the compound of formula (I') and the compound of formula (I'') to produce the compound of formula (I) or the compound of formula (II):

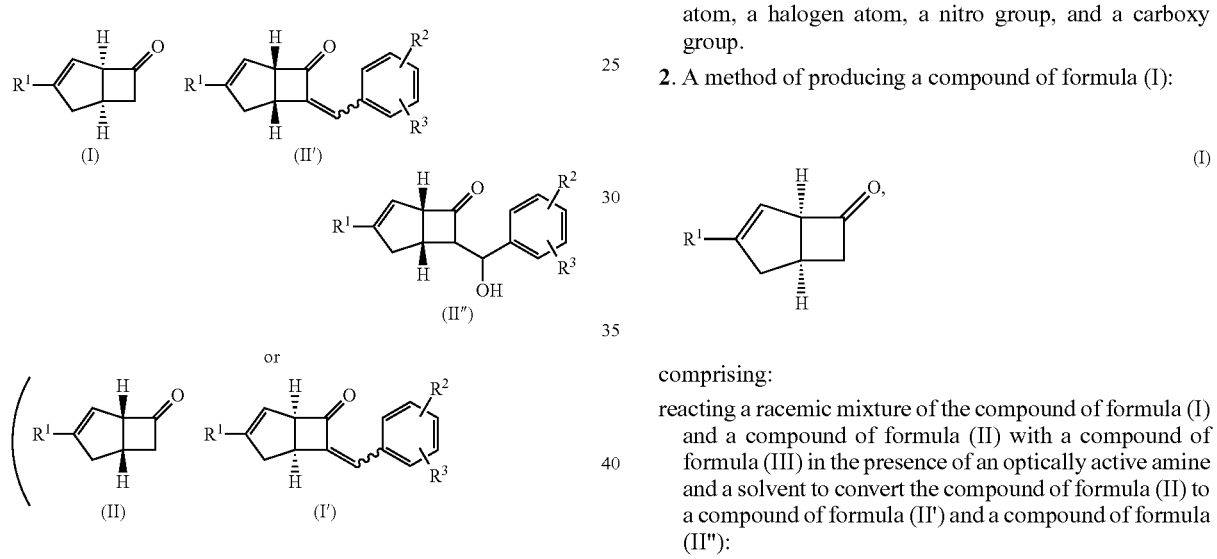

wherein $R^1$ is a hydrogen atom or a C1-C6 alkyl group; and $R^2$ and $R^3$ are independently selected from a hydrogen atom, a halogen atom, a nitro group, and a carboxy group.

2. A method of producing a compound of formula (I):

(I)

comprising:

reacting a racemic mixture of the compound of formula (I) and a compound of formula (II) with a compound of formula (III) in the presence of an optically active amine and a solvent to convert the compound of formula (II) to a compound of formula (II') and a compound of formula (II''):

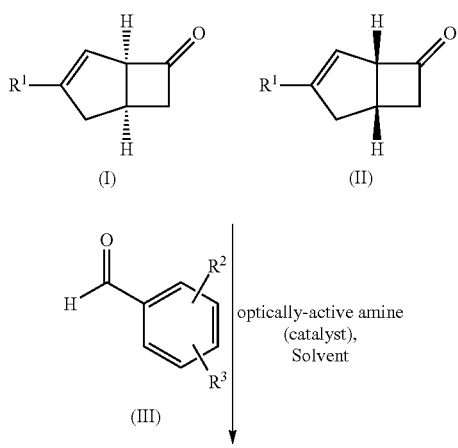

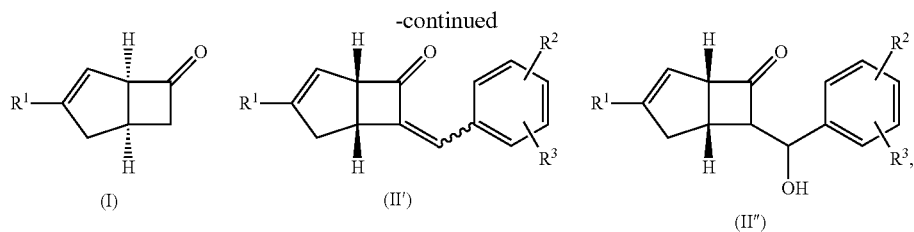

and separating the compound of formula (I) from the compound of formula (II') and the compound of formula (II'') to produce the compound of formula (I):

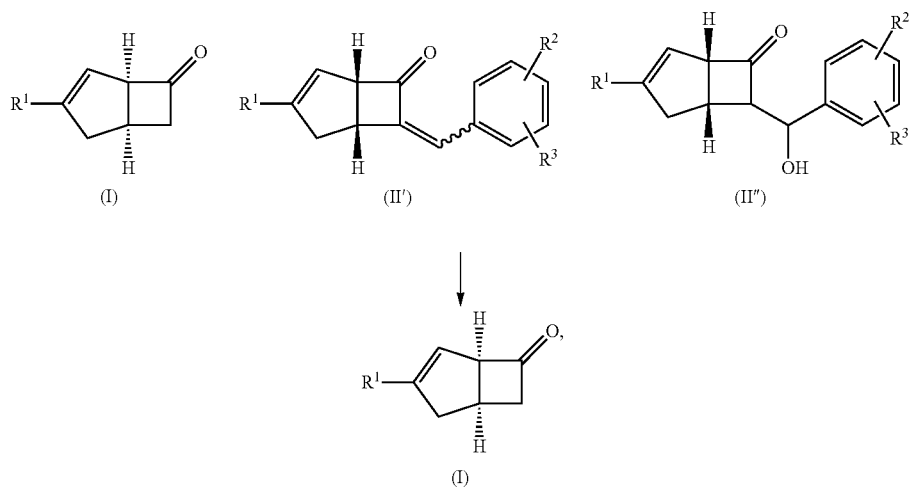

wherein $R^1$ is a hydrogen atom or a C1-C6 alkyl group; and
$R^2$ and $R^3$ are independently selected from a hydrogen atom, a halogen atom, a nitro group, and a carboxy group.

3. The method of claim 1, wherein $R^1$ is a hydrogen atom, a methyl group, or an ethyl group.

4. The method of claim 1, wherein $R^2$ is a hydrogen atom, and $R^3$ is a carboxy group.

5. The method of claim 1, wherein the compound of formula (III) is used in an amount of 0.5 to 2.0 equivalents with respect to the racemic mixture of the compound of formula (I) and the compound of formula (II).

6. The method of claim 2, wherein the optically active amine is selected from the following:

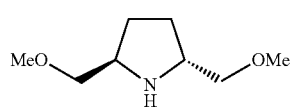

(1-1)

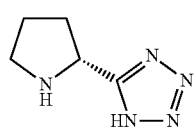

(1-2)

-continued

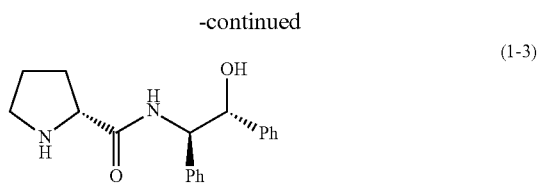

(1-3)

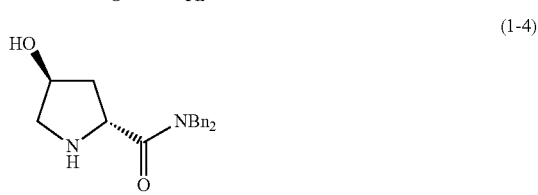

(1-4)

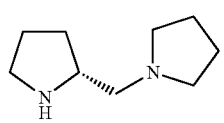

(1-5)

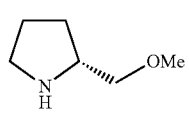

(1-6)

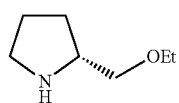

(1-7)

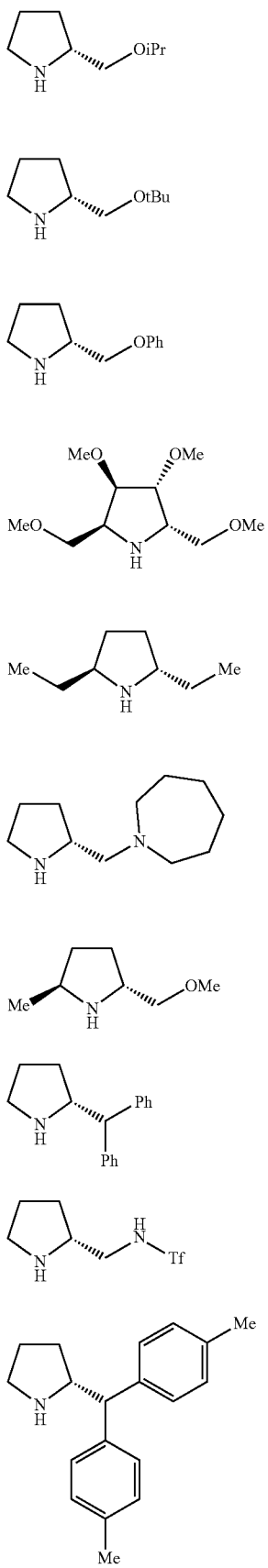

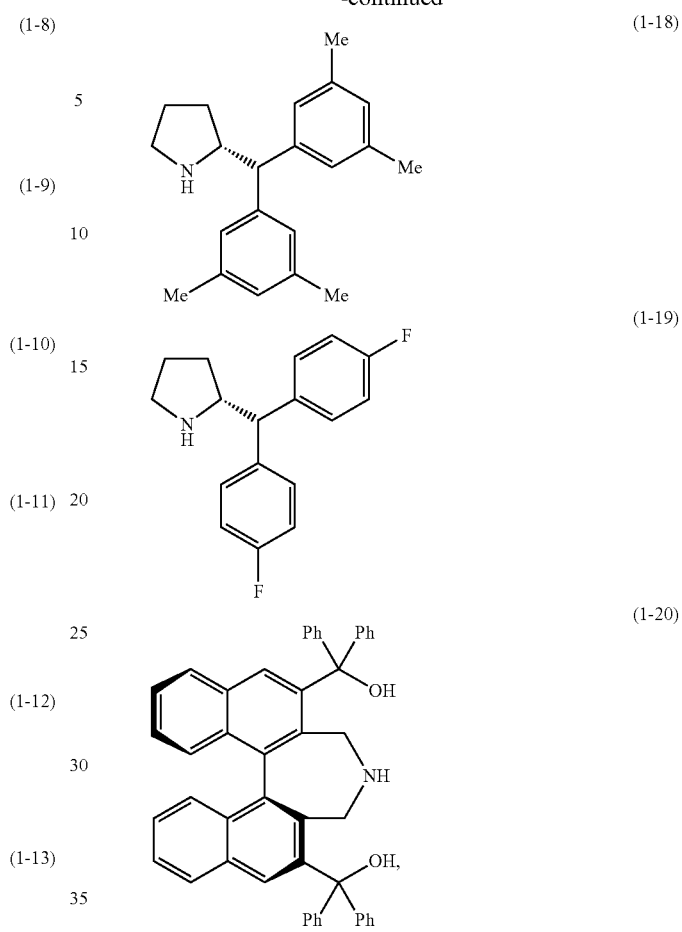

wherein:
Me is a methyl group,
Ph is a phenyl group,
Bn is a benzyl group,
Et is an ethyl group,
iPr is an isopropyl group,
tBu is a tertiary butyl group, and
Tf is a trifluoromethanesulfonyl group.

7. The method of claim 1, wherein the optically active amine is used in an amount of 0.01 to 0.3 equivalents with respect to the racemic mixture of the compound of formula (I) and the compound of formula (II).

8. The method of claim 1, wherein the solvent is selected from acetonitrile, 2-propanol, tetrahydrofuran, 1,2-dimethoxyethane, dimethylacetamide, dimethylformamide, N-methyl-2-pyrrolidone, 1,3-dimethyl-2-imidazolidinone, and dimethyl sulfoxide.

9. The method of claim 1, wherein the reaction of the racemic mixture of the compound of formula (I) and the compound of formula (II) with the compound of formula (III) in the presence of the optically active amine and the solvent further comprises a base.

10. The method of claim 9, wherein the base is selected from potassium phosphate, triethylamine, tributylamine, diisopropylethylamine, 4-methylmorpholine, pyridine, tetramethylethylenediamine, N-methylimidazole, 1,8-diazabicyclo[5.4.0]undec-7-ene, 1,4-diazabicyclo[2.2.2]octane, 4-picoline, 2,6-lutidine, N-methylpyrrole, N-methylpyrrolidine, N-methylpiperidine, and diethylaniline.

11. The method of according to claim 2, futher comprising reacting the compound of formula (I) to produce the compound of formula (IV):

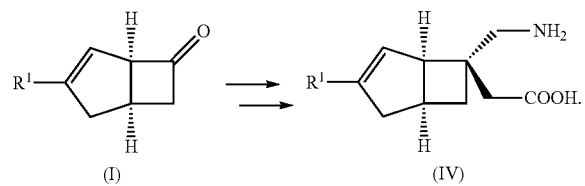

12. The method of claim 2, wherein R¹ is a hydrogen atom, a methyl group, or an ethyl group.

13. The method of claim 2, wherein R² is a hydrogen atom, and R³ is a carboxy group.

14. The method of claim 2, wherein the compound of formula (III) is used in an amount of 0.5 to 2.0 equivalents with respect to the racemic mixture of the compound of formula (I) and the compound of formula (II).

15. The method of claim 2, wherein the optically active amine is used in an amount of 0.01 to 0.3 equivalents with respect to the racemic mixture of the compound of formula (I) and the compound of formula (II).

16. The method of claim 2, wherein the solvent is selected from acetonitrile, 2-propanol, tetrahydrofuran, 1,2-dimethoxyethane, dimethylacetamide, dimethylformamide, N-methyl-2-pyrrolidone, 1,3-dimethyl-2-imidazolidinone, and dimethyl sulfoxide.

17. The method of claim 2, wherein the reaction of the racemic mixture of the compound of formula (I) and the compound of formula (II) with the compound of formula (III) in the presence of the optically active amine and the solvent further comprises a base.

18. The method of claim 17, wherein the base is selected from potassium phosphate, triethylamine, tributylamine, diisopropylethylamine, 4-methylmorpholine, pyridine, tetramethylethylenediamine, N-methylimidazole, 1,8-diazabicyclo[5.4.0]undec-7-ene, 1,4-diazabicyclo[2.2.2]octane, 4-picoline, 2,6-lutidine, N-methylpyrrole, N-methylpyrrolidine, N-methylpiperidine, and diethylaniline.

* * * * *